(12) United States Patent
Pravongviengkham et al.

(10) Patent No.: US 8,945,058 B2
(45) Date of Patent: Feb. 3, 2015

(54) TROCAR CANNULA WITH ATRAUMATIC TIP

(75) Inventors: Kennii Pravongviengkham, Garden Grove, CA (US); Henry Kahle, Trabuco Canyon, CA (US); Jeremy J. Albrecht, Ladera Ranch, CA (US); Scott V. Taylor, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 406 days.

(21) Appl. No.: 12/445,263

(22) PCT Filed: Nov. 21, 2007

(86) PCT No.: PCT/US2007/085444
§ 371 (c)(1),
(2), (4) Date: Apr. 10, 2009

(87) PCT Pub. No.: WO2008/064344
PCT Pub. Date: May 29, 2008

(65) Prior Publication Data
US 2010/0100045 A1    Apr. 22, 2010

Related U.S. Application Data

(60) Provisional application No. 60/866,939, filed on Nov. 22, 2006.

(51) Int. Cl.
A61B 17/34 (2006.01)
A61B 17/00 (2006.01)
A61B 19/00 (2006.01)

(52) U.S. Cl.
CPC ......... *A61B 17/3421* (2013.01); *A61B 17/3494* (2013.01); *A61B 2017/00473* (2013.01); *A61B 2017/3441* (2013.01); *A61B 2019/481* (2013.01)
USPC .................. 604/164.09; 604/164.01; 604/535

(58) Field of Classification Search
CPC ..................... A61M 25/0054; A61M 25/0063; A61M 25/0067; A61M 25/0068; A61M 25/0069
USPC .......... 604/164.01, 164.06, 164.09, 523, 252, 604/533–535
See application file for complete search history.

(56) References Cited

U.S. PATENT DOCUMENTS

| 3,959,429 A | 5/1976 | Benning |
| 4,385,635 A | 5/1983 | Ruiz |

(Continued)

FOREIGN PATENT DOCUMENTS

| EP | 0 192 576 | 8/1986 |
| EP | 0 520 692 | 12/1992 |

(Continued)

OTHER PUBLICATIONS

The International Bureau of WIPO, International Preliminary Report on Patentability for International Application No. PCT/US2007/085444, entitled Trocar Cannual with Atraumatic Tip, dated May 26, 2009.

(Continued)

*Primary Examiner* — Laura Bouchelle
(74) *Attorney, Agent, or Firm* — John Heal

(57) ABSTRACT

A surgical access port is provided with a trocar cannula having a substantially rigid portion and an atraumatic distal tip. The atraumatic distal tip is substantially compliant relative to the rigid portion of the cannula. The trocar cannula provides unobstructed surgical access into a body cavity allowing the insertion and removal of surgical instruments through the trocar cannula and into the body cavity using a minimal sized incision or entryway.

36 Claims, 8 Drawing Sheets

(56) References Cited

U.S. PATENT DOCUMENTS

| | | | | |
|---|---|---|---|---|
| 4,402,684 | A | 9/1983 | Jessup | |
| 4,531,943 | A | 7/1985 | Van Tassel et al. | |
| 4,563,181 | A | 1/1986 | Wijayarathna et al. | |
| 4,776,844 | A | 10/1988 | Ueda | |
| 4,795,426 | A | 1/1989 | Jones | |
| 4,801,297 | A | 1/1989 | Mueller | |
| 4,863,442 | A | 9/1989 | DeMello | |
| 4,875,468 | A | 10/1989 | Krauter et al. | |
| 4,886,506 | A | 12/1989 | Lovgren et al. | |
| 4,950,257 | A | 8/1990 | Hibbs et al. | |
| 5,017,259 | A | 5/1991 | Kohsai | |
| 5,045,072 | A | 9/1991 | Castillo et al. | |
| 5,049,138 | A * | 9/1991 | Chevalier et al. | 604/265 |
| 5,078,702 | A | 1/1992 | Pomeranz | |
| 5,120,317 | A | 6/1992 | Luther | |
| 5,179,934 | A | 1/1993 | Nagayoshi et al. | |
| 5,221,270 | A | 6/1993 | Parker | |
| 5,234,416 | A | 8/1993 | Macaulay et al. | |
| 5,240,537 | A | 8/1993 | Bodicky | |
| 5,257,973 | A | 11/1993 | Villasuso | |
| 5,257,980 | A | 11/1993 | Van Antwerp et al. | |
| 5,295,994 | A | 3/1994 | Bonutti | |
| 5,300,032 | A | 4/1994 | Hibbs et al. | |
| 5,318,032 | A | 6/1994 | Lonsbury et al. | |
| 5,417,665 | A | 5/1995 | De La Mata et al. | |
| 5,450,842 | A | 9/1995 | Tovey et al. | |
| 5,509,910 | A | 4/1996 | Lunn | |
| 5,533,985 | A | 7/1996 | Wang | |
| 5,542,924 | A | 8/1996 | Snoke et al. | |
| 5,584,821 | A | 12/1996 | Hobbs et al. | |
| 5,599,319 | A | 2/1997 | Stevens | |
| 5,752,970 | A | 5/1998 | Yoon | |
| 5,762,637 | A | 6/1998 | Berg et al. | |
| 5,769,830 | A | 6/1998 | Parker | |
| 5,800,451 | A | 9/1998 | Buess et al. | |
| 5,911,715 | A | 6/1999 | Berg et al. | |
| 5,935,107 | A * | 8/1999 | Taylor et al. | 604/164.04 |
| 6,015,403 | A | 1/2000 | Jones | |
| 6,077,258 | A | 6/2000 | Lange et al. | |
| 6,171,282 | B1 | 1/2001 | Ragsdale | |
| 6,245,053 | B1 | 6/2001 | Benjamin | |
| 6,273,869 | B1 | 8/2001 | Vaillancourt | |
| 6,491,670 | B1 | 12/2002 | Toth et al. | |
| 6,533,770 | B1 | 3/2003 | Lepulu et al. | |
| 6,613,038 | B2 | 9/2003 | Bonutti et al. | |
| 6,800,076 | B2 | 10/2004 | Humayun | |
| 6,866,655 | B2 | 3/2005 | Hackett | |
| 6,893,427 | B1 | 5/2005 | Jimenez | |
| 6,964,750 | B2 | 11/2005 | Fulford | |
| 7,083,626 | B2 * | 8/2006 | Hart et al. | 606/108 |
| 7,115,134 | B2 | 10/2006 | Chambers | |
| 7,390,317 | B2 * | 6/2008 | Taylor et al. | 604/167.06 |
| 7,591,802 | B2 * | 9/2009 | Johnson et al. | 604/167.06 |
| 2002/0002343 | A1 * | 1/2002 | Hung et al. | 600/573 |
| 2003/0004528 | A1 | 1/2003 | Ishikawa | |
| 2004/0049158 | A1 * | 3/2004 | Ley et al. | 604/167.03 |
| 2004/0077928 | A1 | 4/2004 | Moriyama | |
| 2004/0106942 | A1 * | 6/2004 | Taylor et al. | 606/185 |
| 2004/0158230 | A1 | 8/2004 | Hunn et al. | |
| 2005/0033272 | A1 | 2/2005 | Humayun | |
| 2005/0059934 | A1 | 3/2005 | Wenchell et al. | |
| 2005/0137524 | A1 | 6/2005 | Sakal et al. | |
| 2005/0165366 | A1 | 7/2005 | Brustad et al. | |
| 2005/0203342 | A1 | 9/2005 | Kucklick et al. | |
| 2005/0209619 | A1 | 9/2005 | Johnson et al. | |
| 2005/0216028 | A1 | 9/2005 | Hart et al. | |
| 2005/0251191 | A1 * | 11/2005 | Taylor et al. | 606/190 |
| 2005/0256452 | A1 | 11/2005 | DeMarchi et al. | |
| 2006/0229637 | A1 * | 10/2006 | Hart et al. | 606/108 |
| 2007/0088277 | A1 * | 4/2007 | McGinley et al. | 604/167.01 |
| 2007/0225650 | A1 * | 9/2007 | Hart et al. | 604/174 |
| 2008/0077169 | A1 * | 3/2008 | Taylor et al. | 606/185 |
| 2008/0091143 | A1 * | 4/2008 | Taylor et al. | 604/167.05 |
| 2008/0249475 | A1 * | 10/2008 | Albrecht et al. | 604/167.06 |
| 2009/0065662 | A1 * | 3/2009 | Taylor | 248/156 |
| 2009/0192444 | A1 * | 7/2009 | Albrecht et al. | 604/26 |
| 2009/0221960 | A1 * | 9/2009 | Albrecht et al. | 604/103.03 |

FOREIGN PATENT DOCUMENTS

| | | |
|---|---|---|
| EP | 0 916 359 | 5/1999 |
| EP | 1 557 130 A1 | 7/2005 |
| EP | 1 854 421 | 11/2007 |
| GB | 2 425 483 | 11/2006 |
| JP | 5-337076 | 12/1993 |
| JP | 7-148171 | 6/1995 |
| JP | 7-184846 | 7/1995 |
| WO | WO 97/17888 | 5/1997 |
| WO | WO 03/088854 | 10/2003 |
| WO | WO 2006/019714 | 2/2006 |

OTHER PUBLICATIONS

European Patent Office, The International Search Report and Written Opinion for International Application No. PCT/US2007/085444, entitled Trocar Cannual with Atramatic Tip, dated Oct. 17, 2008.

European Patent Office, European Search Report for European Patent Application No. EP12164164, entitled "Trocar Cannula With Atraumatic Tip", dated May 29, 2012.

* cited by examiner

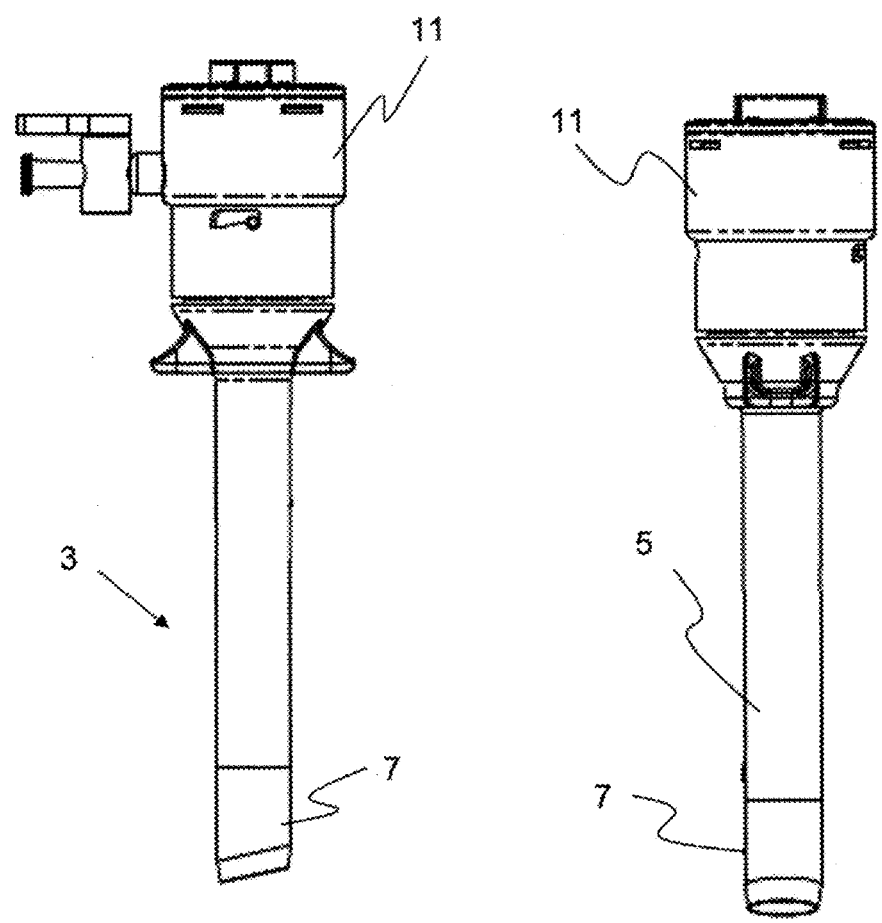

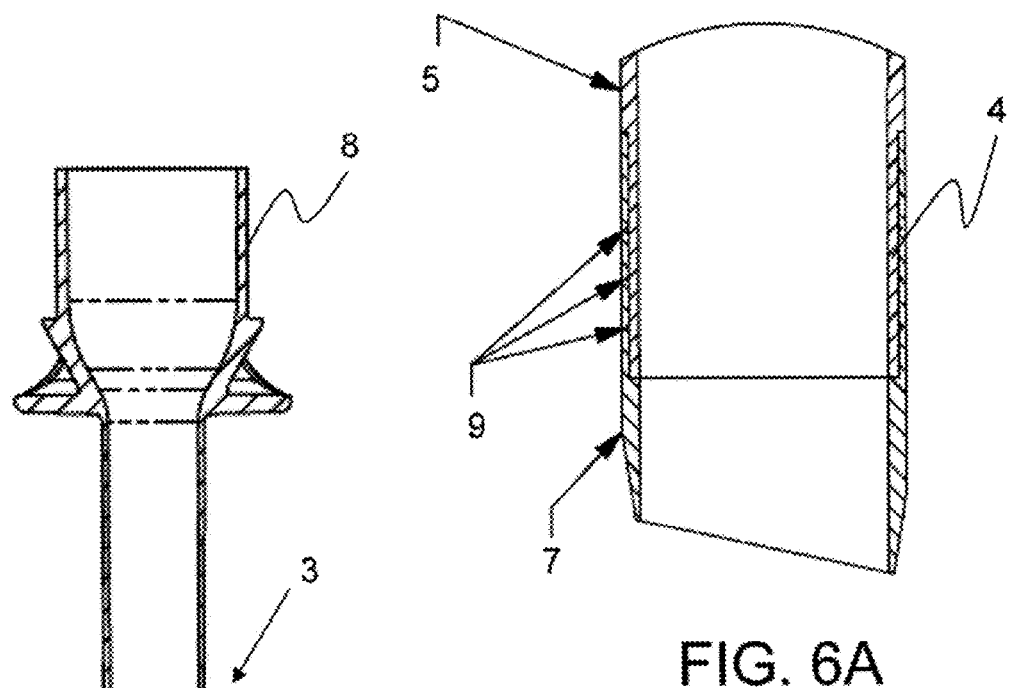
FIG. 6A
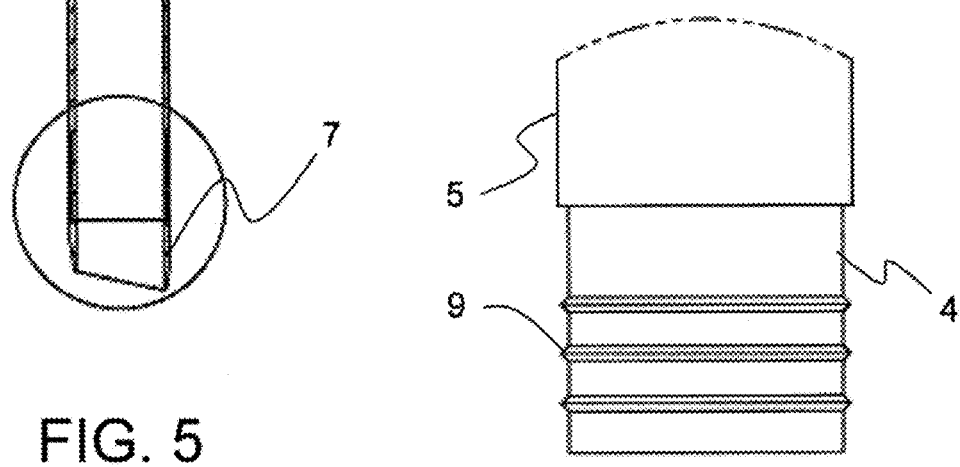
FIG. 5
FIG. 6B

TROCAR CANNULA WITH ATRAUMATIC TIP

CROSS-REFERENCE TO RELATED APPLICATIONS

This application is a national stage filing under 35 U.S.C. §371 of International Application No. PCT/US2007/85444 entitled "TROCAR CANNULA WITH ATRAUMATIC TIP" filed on Nov. 21, 2007, which claims the benefit of U.S. Provisional Patent Application No. 60/866,939, filed on Nov. 22, 2006, the entire disclosure of which is hereby incorporated by reference as if set forth in full herein.

BACKGROUND

This invention generally relates to medical access devices and, more specifically, to a trocar cannula with an atraumatic tip.

During use of a trocar in a surgical procedure, such as a laparoscopic procedure, a trocar is placed across the abdominal wall and the trocar cannula is left disposed across the abdominal wall. The distal tip of the cannula is positioned on the anterior side of the abdominal wall. Laparoscopic procedures can utilize several trocars across the abdominal wall and therefore several cannulas may be disposed across the abdominal wall at the same time. With several cannulas disposed across the abdominal wall, it can be difficult to constantly observe and monitor the positioning of the distal tips of the cannulas while the laparoscopic procedure is being conducted. For example, because of the number of cannulas disposed across an abdominal wall in a laparoscopic procedure, it is possible for a cannula tip to unintentionally engage body tissue out of the surgeon's field of view provided by the laparoscope and camera. The trocar in accordance with aspects of the present invention minimizes the possibility for a trocar cannula to inadvertently engage and traumatize body tissue in a body cavity, due to accidental misuse, for example, by providing a cannula with a distal tip, which is elastomeric, compliant, soft, and generally atraumatic.

SUMMARY

In one aspect, a trocar cannula comprises a elongate body having a proximal enlarged end and a distal tip end with a lumen extending from the proximal end to the distal end for inserting and removing surgical instruments through the lumen and an atraumatic tip integrated with and extending from the distal tip end of the elongate body, the tip being more compliant than the elongate body and formed from a material different from the elongate body.

In one aspect, a trocar cannula comprises a elongate body having a proximal enlarged end and a distal tip end with a lumen extending from the proximal end to the distal end for inserting and removing surgical instruments through the lumen and a flexible joint integrated with and extending from the distal tip end of the elongate body, the flexible joint being more compliant than the elongate body and formed from a material different from the elongate body. A tip is integrated with and extends from an opposing end of the flexible joint away from the distal tip end of the elongate body, the tip being less compliant than the flexible joint and being formed from a material different from the flexible joint.

In one aspect, a trocar cannula comprises a trocar seal housing having an instrument seal and a zero seal contained within the trocar seal housing, a elongate body having a proximal enlarged end having projections extending from an outer surface of the proximal enlarged end, a distal tip end having annular projections and a lumen extending from the proximal enlarged end to the distal tip end for inserting and removing surgical instruments through the lumen, the trocar seal housing releasably connected to plurality of projections of the proximal enlarged end with the zero seal situated within the proximal enlarged end and the instrument seal situated within the zero seal and an atraumatic tip fixedly interlocked with the annular projections of the distal tip end of the elongate body, the tip being deformable, formed from a material different from the elongate body and having a flexural modulus of about 1,500 psi and an ultimate elongation of about 400%, and the elongate body having a flexural modulus substantially greater than the flexural modulus of the tip and an ultimate elongation substantially less than the ultimate elongation of the tip.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIGS. 1-2 are side views of a trocar system in accordance with various aspects of the present invention;

FIG. 5 is a cross-sectional side view of a trocar cannula in accordance with various aspects of the present invention;

FIG. 6A is an enlarged cross-sectional side view of a portion of a trocar cannula in accordance with various aspects of the present invention;

FIG. 6B is an enlarged side view of a portion of a trocar cannula without a tip in accordance with various aspects of the present invention;

DETAILED DESCRIPTION

Figure 3:
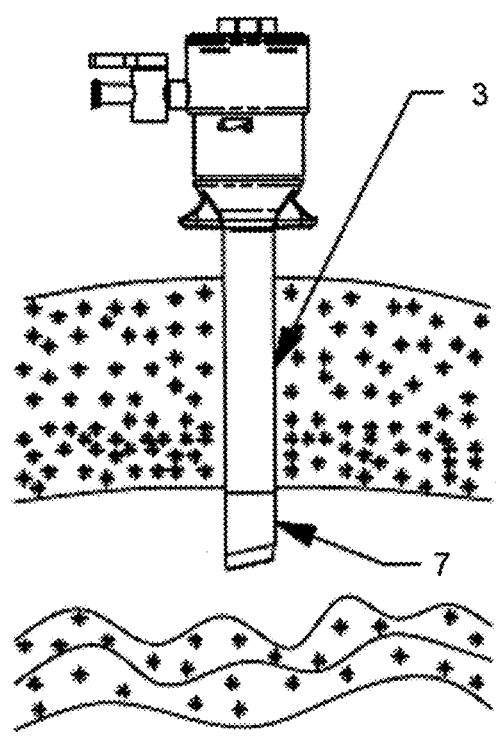
FIGS. 3-4 are side views of an operational use of a trocar system in accordance with various aspects of the present invention.
Figure 4:
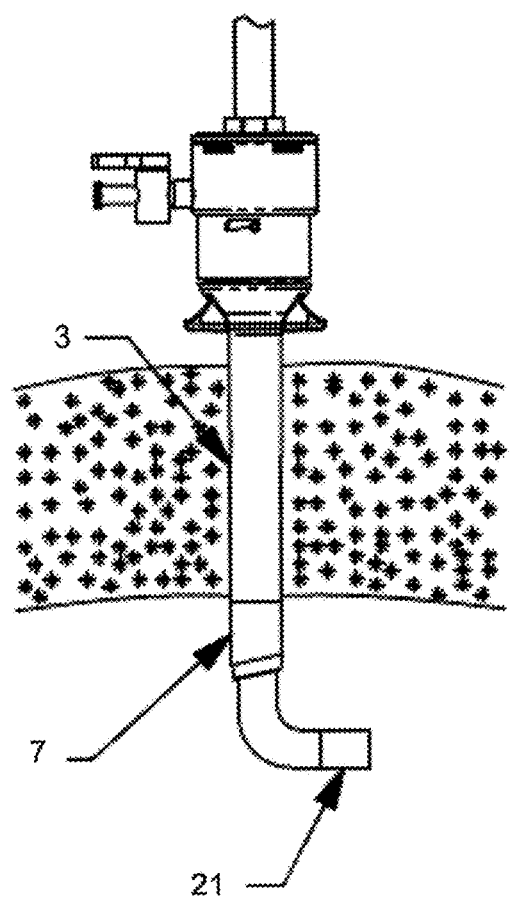

Generally, an access port or trocar is provided with a cannula having an atraumatic distal tip. The trocar is used during minimally invasive surgery to provide an access channel into the body through which a surgeon may insert medical instruments. The cannula in one aspect has a proximal portion, which is formed of a rigid polymer and a distal portion formed of an elastomeric polymer. The elastomeric cannula tip has sufficient column strength to enable passage through a body wall when used in combination with an obturator yet has a lower durometer hardness and is more compliant as compared to the proximal portion of the cannula. The low durometer and compliance of the atraumatic cannula tip prevents the cannula tip from potentially traumatizing, due to accidental misuse, for example, or engaging adjacent body tissue during a surgical procedure such as a laparoscopic procedure. Some trocar cannulas are typically formed of a single material such as stainless steel or polycarbonate. These trocar cannulas can be rigid and include tapered distal tips, which can engage body tissue and may cause trauma to the engaged body tissue, due to, for example, accidental misuse.

Referring to FIGS. 1-14, a surgical access port, e.g., a trocar, which comprises a trocar seal housing 11, a trocar cannula 3, and/or an obturator is provided. In this description, "proximal" or "proximally" refers to that portion of the instrument, component, or element that extends toward the user. "Distal" or "distally" refers to that portion of the instrument, component, or element that extends away from the user. The trocar is configured to access a body cavity and to maintain positive pressure at its distal end to prevent loss of surgical insufflation gas such as carbon dioxide used, for example, in laparoscopic procedures to insuffiate the body cavity. The trocar seal and trocar cannula is also configured to sealingly engage surgical instruments of various diameters, which would typically be inserted through the trocar, to prevent loss of surgical gas during use of such instruments and/or when no instrument is inserted. In one aspect, the trocar seal housing is releasably attachable to the trocar cannula to allow the seal to be removed during surgery to enable the extraction of tissue specimens through the trocar. The trocar in one aspect has or is included with an optical obturator having a tip, which includes a smooth outer surface and has a high degree of optical clarity.

The trocar seal housing 11 in one aspect can be easily detached or removed from a proximal enlarged end of the trocar cannula 3 and easily attached or re-attached to the trocar cannula 3 for example during a surgical procedure. During surgery, small tissue specimens may be extracted from a body cavity through a trocar to enable pathological analysis of the tissue specimen. The integrity of the tissue specimen can be maintained or the maintenance facilitated by avoiding or minimizing withdrawal of delicate tissue specimens through a trocar seal. As such, in one aspect, the trocar seal housing 11 is arranged to be removed from the trocar cannula 3 to enable extraction of tissue specimens from a body cavity while maintaining the integrity of the tissue specimen. The trocar seal housing 11 also easily reattaches to the trocar cannula 3 after its initial removal during a surgical procedure.

Laparoscopic surgery of the abdominal area typically requires the introduction of an insufflation gas into the peritoneal cavity of the patient. The insufflation gas is usually pressurized to about 10 mm Hg above atmospheric pressure. This in turn lifts the abdominal wall away from the organs underlying it. Pressurized insufflation gas in one aspect is introduced through the stopcock of the trocar seal housing 11 into the trocar cannula 3. Trocar seal housing 11, accommodating instrument and/or zero seals, prevents the gas from escaping proximally out from the cannula 3 and allows the insertion and removal of a laparoscope and surgical instruments into and out of the surgical site.

Also, in one aspect, the trocar seal housing 11 is easily removable from the trocar cannula 3 to enable rapid desufflation of an insufflated body cavity. In one aspect, a trocar lock releasably attaches the trocar cannula to the trocar seal housing. For example, towards the end of a laparoscopic surgical procedure, release of the insufflation gas such as carbon dioxide from the peritoneal cavity of the patient is performed. By opening one or more stopcock valves on the trocar seal, desufflation can be achieved. The flow rate through the stopcock valves, however, can be slow with regard to evacuation of the carbon dioxide from the peritoneal cavity and therefore the time expended to evacuate the insufflation gas can be excessive. By removing the seal housing 11 from the cannula 11, the cannula provides an unobstructed outlet for the insufflation gas to escape thereby decreasing desufflation time.

During an operational exemplary use, a laparoscope 21 is inserted into and through trocar seal housing 11 and into cannula 3. An endoscopic video camera is attached to the proximal end of the laparoscope. As the surgeon advances the trocar through the body wall, the surgeon can visually observe the tissue through the laparoscope via a video monitor, which is connected to the endoscopic video camera.

Referring to FIGS. 1-6, the trocar system, i.e., a surgical access port for entry into a body cavity, in one aspect is provided in that an atraumatic distal tip 7 of a trocar cannula 3 prevents or minimizes potentially destructive engagement with laparoscopic instrumentation such as an articulating laparoscope 21. For example, if an articulating laparoscope is placed through a typical cannula, the distal tip of the laparoscope then articulated, and the laparoscope then withdrawn from the cannula, the flexible joint of the laparoscope can contact the distal tip of the cannula resulting in damage to the flexible joint of the laparoscope. The damage to the laparoscope may be such as to require immediate replacement of the laparoscope resulting in an immediate delay in the surgical procedure. Articulating laparoscopes are also typically very expensive in comparison with non-articulating laparoscopes and therefore, it can be very costly for a hospital or a manufacturer to replace or repair a damaged articulating laparoscope. The trocar in accordance with one aspect of the present invention addresses this by providing a cannula 3 with an elastomeric distal tip 7, which is compliant, and has a low durometer. The atraumatic elastomeric distal tip 7 on the cannula 3 in one aspect is sufficiently compliant and soft so as to prevent or minimize potential damage to instrumentation, which engages the cannula tip 7 during withdrawal of the instrumentation.

In one aspect, the cannula 3 with the atraumatic tip 7 is a high durometer rigid polymer cannula formed of a material such as polycarbonate. The atraumatic tip comprises a low durometer elastomeric material such as polyurethane. The cannula in one aspect is injection molded and the atraumatic elastomeric tip is then over-molded onto a distal tip end of an elongate body of the cannula. The atraumatic tip is held in place via a mechanical interlock fit. The mechanical interlock fit includes a plurality of annular ribs 9 on the cannula tip 4, which are over-molded with the atraumatic elastomeric tip 7. The annular ribs 9 prevent or resist axial movement of the atraumatic elastomeric tip 7 relative to the rigid polycarbonate cannula. The length of the atraumatic elastomeric tip 7 can range from approximately 0.25" to approximately 1" long. This length enables the cannula 3 to be disposed across the abdominal wall such that the rigid portion 5 of the cannula 3 is positioned within the abdominal wall to hold the abdominal wall in a retracted position. The retracted abdominal wall also serves to aid with anchoring the cannula 3 in place and prevents axial movement of the cannula during the surgical procedure. The atraumatic elastomeric tip 7 is positioned within the peritoneal cavity and in one aspect is the only portion of the cannula to be disposed within the peritoneal cavity.

In one aspect, the cannula tip or distal tip end 4 of the cannula has a wall thickness smaller than remaining portions of the cannula 3. A proximal portion of the atraumatic tip 7 has a wall thickness substantially similar to cannula tip 4 and in one aspect, a distal portion of the atraumatic tip 7 has a wall thickness substantially similar to a wall thickness of a proximal portion of the cannula 3. In one aspect, the atraumatic elastomeric tip 7 is formed from a material, e.g., a transparent polyurethane material, or otherwise configured/arranged to ensure that visibility through the tip is maintained. The transparent elastomeric tip assists in positioning the cannula 3 within the abdominal wall. By placing the laparoscope lens just proximal to the tip of the cannula 3, the abdominal wall can be viewed through the cannula tip 6 while positioning the cannula such that only the atraumatic elastomeric tip 7 of the cannula is disposed within the peritoneal cavity. The atraumatic elastomeric tip 7 in one aspect is formed with a contrasting tint as compared to the rigid portion 5 of the cannula to further aid with positioning of the cannula within the abdominal wall and the peritoneal cavity.

In one aspect, the rigid portion 5 of the cannula 3 is formed from polyethylene, polysulfone, polyethersulfone, polyetherimide, polycarbonate, polyurethane, liquid crystal polymer, nylon, polyester, polypropylene, or ABS (Acrylonitrile Butadiene Styrene). In one aspect, the atraumatic elastomeric tip portion of the cannula is formed from silicone, polyurethane, polyester, polystyrene, nylon, polyvinyl chloride, mylar, polyethylene, Kraton® thermoplastic elastomers, C-Flex® thermoplastic elastomers, Versaflex® thermoplastic elastomers, Santoprene® thermoplastic elastomers, Carbothane® thermoplastic polyurethanes, copolymer/mineral oil gels, polyisoprene, or natural rubber.

In one aspect, the cannula 3 has an ultimate elongation less than the ultimate elongation of the atraumatic tip 7. For example, the ultimate elongation of the cannula 3 is about 120% versus the ultimate elongation of the atraumatic tip 7 being about 410%. In one aspect, the ultimate elongation of the cannula 3 is within the range of about 2% to about 150% versus the ultimate elongation of the atraumatic tip 7 being in the range of about 300% to about 1,000%. In one aspect, the ultimate elongation of the tip is at least three times greater than the ultimate elongation of the cannula. The large or greater ultimate elongation of the tip ensures that the tip does not tear off when a surgical instrument is inserted through the cannula, moved off-axis and/or portions of the instrument articulated off-axis relative to the longitudinal axis of the cannula which may interfere and/or damage the instrument and/or tip portions of which may fall into the surgical site.

In one aspect, the atraumatic elastomeric tip 7 of the cannula 3 is formed from an elastomeric material which further softens upon extended exposure to body temperatures. The elastomeric material can therefore be less compliant during the initial insertion of the trocar when lower compliance is used providing a lower insertion force, and upon extended exposure to body temperatures, the atraumatic cannula tip would then soften resulting in a more compliant and therefore a more atraumatic cannula tip. Examples of elastomeric materials with these properties are the Carbothane® thermoplastic polyurethanes available from Noveon.

In one aspect, the cannula 3 with the atraumatic elastomeric tip 7 is provided with inside diameters ranging from 1 mm to 30 mm. A typical wall thickness for the cannula is about 0.25 mm to 1 mm. The cannula with the atraumatic elastomeric tip in one aspect is formed using a dual-shot molding process whereby the rigid portion is first molded and then the elastomeric portion is then over-molded onto the rigid portion using a dual-shot injection mold and a dual-shot injection molding press. In one aspect, the cannula 3 with the atraumatic elastomeric tip 7 can be used in conjunction with non-bladed dilating obturators, non-shielded bladed obturators, shielded bladed obturators, electrosurgical obturators, and blunt tip obturators. In one aspect, the cannula 3 with the atraumatic elastomeric tip 7 can have a semi-rigid or flexible proximal portion to enable placement of the cannula through a body conduit such as a urethra or ureter. The proximal portion of the cannula or catheter would be configured to be less flexible than the distal tip portion of the cannula. In one aspect, the proximal portion 8 of the cannula 3 is enlarged accommodating instrument and/or zero seals, surgical instruments with different diameters and orientation of such instruments, providing finger holds or grips, suture tie slots, and/or a releasable connection to the seal housing 11.

Figure 7:
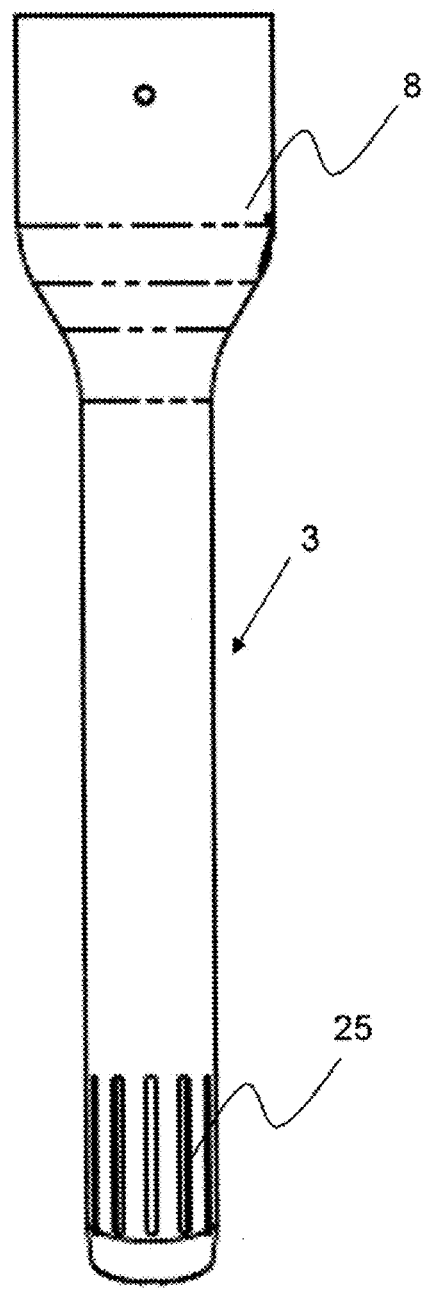
FIG. 7 is a side view of a trocar system in accordance with various aspects of the present invention.
Figure 8:
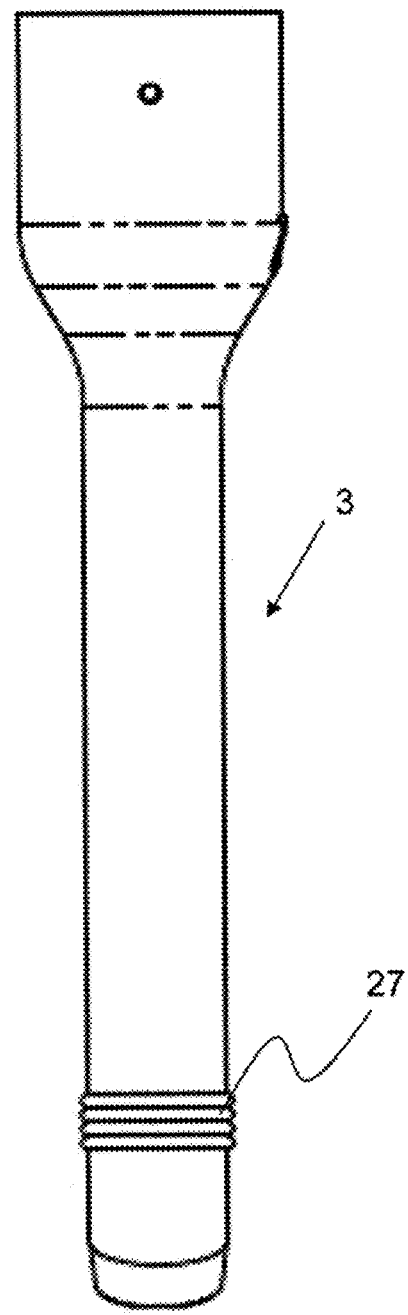
FIG. 8 is a side view of a trocar system in accordance with various aspects of the present invention.

In one aspect, the cannula 3 with the atraumatic elastomeric tip 7 is formed of a single material. The cannula has thinned wall sections or axial slots 25 at its distal tip to provide the distal tip of the cannula with greater flexibility as compared to the proximal portions of the cannula (FIG. 7). In FIG. 8, the cannula in one aspect is formed of a single material with a flexible joint 27 between the proximal portion and the distal portion of the cannula. The flexible joint, e.g., bellows, would enable the distal tip or portion of the cannula to pivot in response to contact with body tissue or inserted instrumentation. In one aspect, the flexible joint 27 integrated with and extending from the proximal portion of the cannula 3. The flexible joint 27 is more compliant than the proximal or rigid portion 5 of the cannula 3 and is formed from a material that is different from the material of the other portions of the cannula 3. The tip or distal portion of the cannula is integrated with and extending from an opposing end of the flexible joint away from the distal tip end of the elongate body. In one aspect, the tip is less compliant than the flexible joint and is formed from a material different from the material of the flexible joint. The tip or distal portion in one aspect is formed from a material corresponding to the material of the proximal portion of cannula 3. In one aspect, the flexible joint is formed of thermoplastic polyurethane and has a flexural modulus substantially smaller than the flexural modulus of the cannula 3.

In one aspect, the atraumatic tip 7 has a flexural modulus that is about 1,500 psi and the flexural modulus of the cannula is about 330,000 psi. In one aspect, the flexural modulus of the cannula is greater than at least 100,000 psi and the tip 7 is less than at least 10,000 psi. In one aspect, the flexural modulus of the atraumatic tip is within the range of about 500 psi to about 15,000 psi versus the cannula is in the range of about 100,000 psi to about 500,000 psi. The flexural modulus of the cannula is about ten times greater than the flexural modulus of the tip. The greater flexural modulus of the tip relative to the cannula allows the tip 7 to deflect, bend and/or deform to avoid unintended contact and complications with tissue/organs and to avoid potential interference and/or damage to flexible or deflectable instruments articulated during a surgical procedure or instruments being withdrawn with portions of the instrument deflected or articulated off-center or alignment with the longitudinal axis of the cannula. The pronounced difference ensures the tip to deflect relative to the cannula allowing the remaining portion to remain still and thus not pull, tear or enlarge the minimally sized surgical incision or entryway. Also, the difference ensures that tip deflects or does not otherwise interfere with a surgical instrument, e.g., a laparoscope, obturator and others, having a tubular portion or shaft with properties similar to the remaining portions of the cannula inserted through the cannula and moved off-axis or portions of the instrument articulated off-axis.

The atraumatic elastomeric tip 7 in one aspect is bonded with an adhesive to the rigid portion of the cannula. The atraumatic elastomeric tip in one aspect is ultrasonically welded or thermally welded to the rigid portion of the cannula. In one aspect, the atraumatic elastomeric tip is formed of a material arranged to chemically bond with the rigid portion 5 of the cannula 3 during injection molding. For example, the cannula 3 may be formed of polypropylene and the elastomeric tip 7 formed of a C-Flex® thermoplastic elastomer specifically formulated to chemically bond to polypropylene during injection molding.

In one aspect, the atraumatic elastomeric tip 7 is coated or treated to reduce the friction associated with the movement of instrumentation when the instrumentation contacts the elastomeric tip. The coating or treatment can also reduce the force used to place the trocar through the abdominal wall. Examples of coatings and treatments include parylene coatings, hydrophilic coatings, plasma surface treatments, and chlorination treatments. In one aspect, the atraumatic elastomeric tip is formed from a radiopaque material. A typical radiopaque material includes barium sulfate as an additive.

Figure 9A:
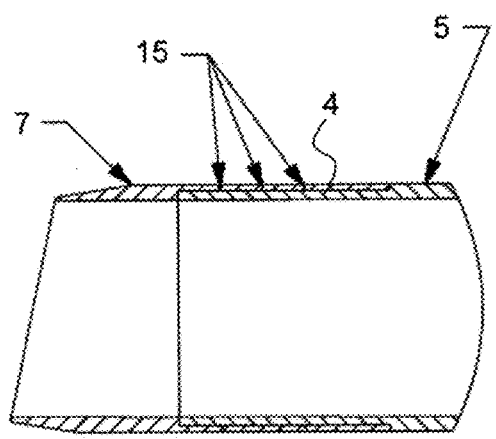
FIG. 9A is an enlarged cross-sectional side view of a portion of a trocar cannula in accordance with various aspects of the present invention.
Figure 9B:
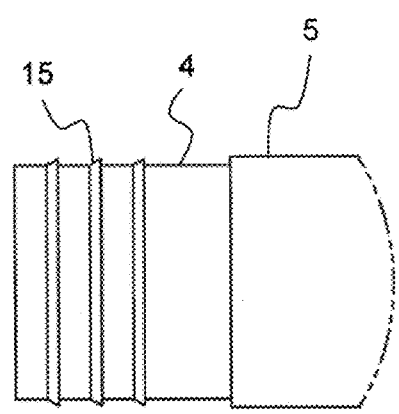
FIG. 9B is an enlarged side view of a portion of a trocar cannula without a tip in accordance with various aspects of the present invention.

Referring now to FIG. 9, in one aspect, the tip of the rigid portion 5 of the cannula 3 is formed with annular barbs 15 to provide a mechanical lock with the over-molded elastomeric tip 7. The tip 4 of the rigid portion 5 of the cannula 3 in one aspect is formed with a series of directionally alternating annular barb configurations, such that the barbs create a mechanical lock increasing axial tension strength of the tip to the rest of the cannula and preventing the elastomeric tip 7 from moving in either a proximal or a distal direction relative to the rigid portion 5 of the cannula 3. The tip 4 of the rigid portion 5 of the cannula 3 in one aspect is formed with annular grooves to provide a mechanical lock with the over-molded elastomeric tip 7. The tip 4 of the rigid portion 5 of the cannula 3 in one aspect is formed with holes and/or axial grooves to provide a mechanical lock with the over-molded elastomeric tip 7. The tip 4 of the rigid portion 5 of the cannula 3, in one aspect, is formed with a thread to provide a mechanical lock with the over-molded elastomeric tip.

Figure 10:
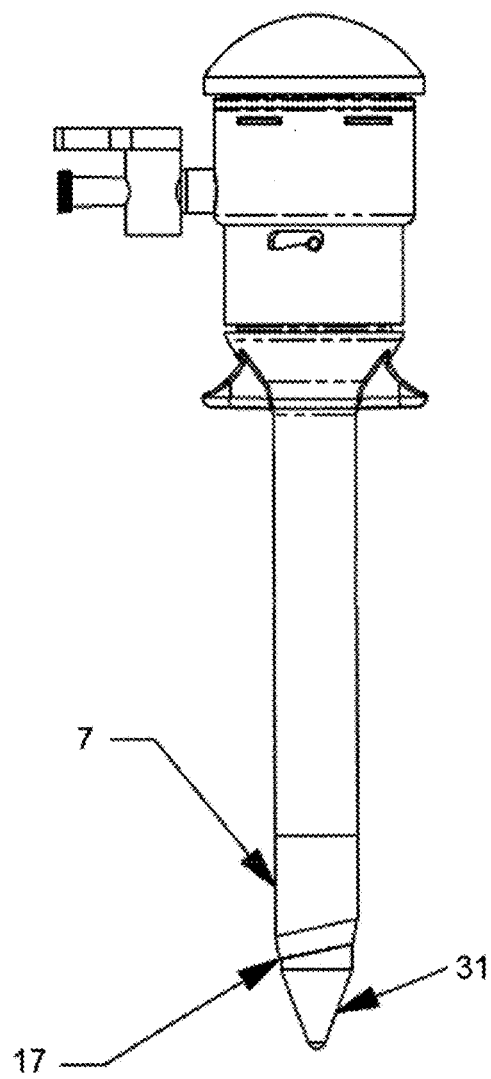
FIG. 10 is a side view of a trocar system in accordance with various aspects of the present invention.
Figure 15:
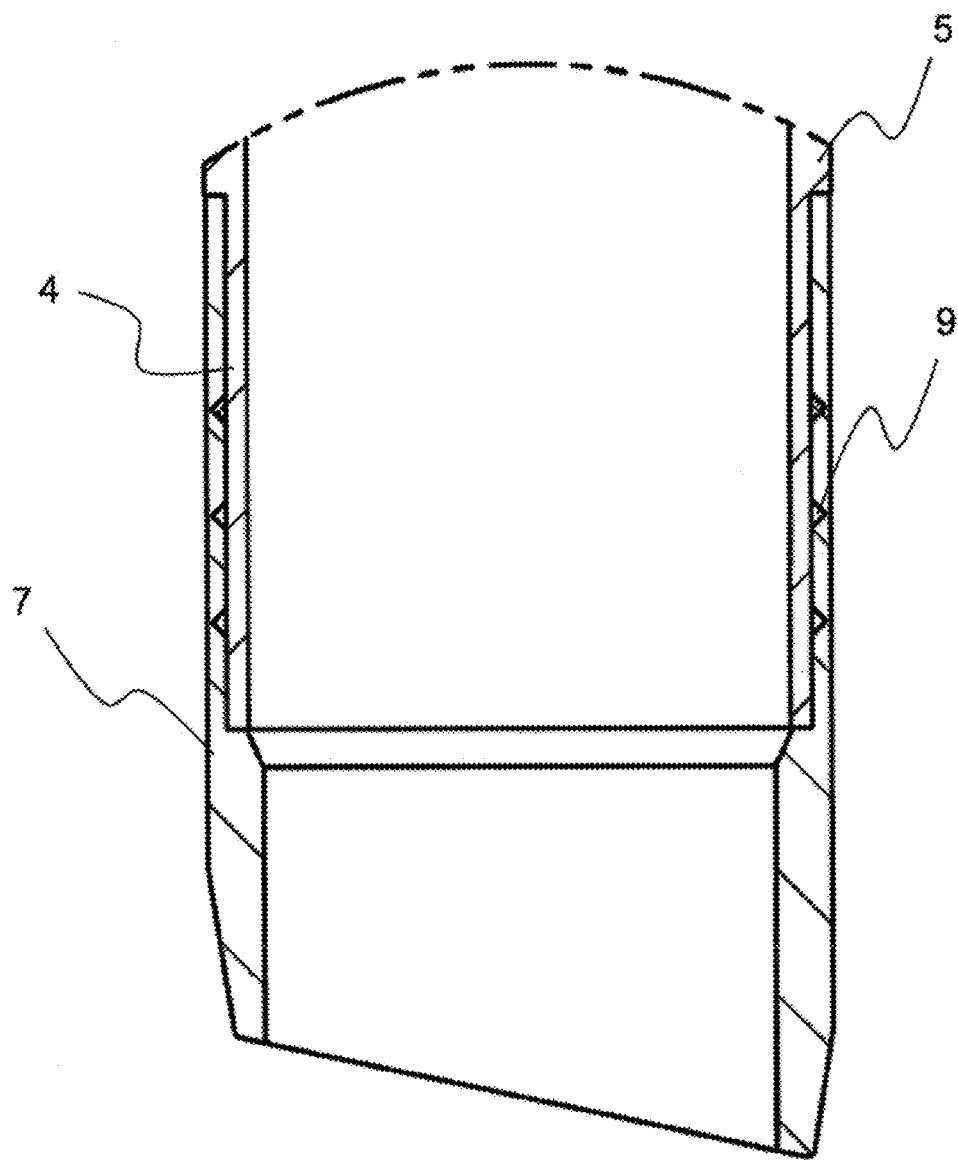
FIG. 15 is an enlarged cross-sectional side view of a portion of a trocar cannula in accordance with various aspects of the present invention.

The inside diameter of a distal tapered portion 17 of the atraumatic elastomeric tip 7 in one aspect is configured to slightly interfere with the outside diameter of an obturator 31 such that when the obturator is inserted into the cannula 3, the obturator expands the elastomeric distal tip of the cannula to create a smooth transition between the distal tip of the cannula and the obturator (FIG. 10). The smooth transition between the distal tip of the cannula and the obturator can decrease the possibility for body tissue to wedge between the cannula and the obturator during insertion through the abdominal wall and can therefore reduce the insertion force required to place the trocar through the abdominal wall. The interference fit can also serve to create a seal between the distal tip of the obturator 31 and the cannula 3. The seal can prevent or minimize insufflation gasses from flowing between the interface of the distal tip of the cannula and the obturator. In one aspect, to facilitate the interference fit, the atraumatic tip 7 has an inner diameter that is less than an inner diameter of the elongate body or distal tip end of the cannula 3. The atraumatic tip 7, in one aspect, is chamfered or tapered narrowing and transitioning from a larger inner diameter corresponding to the inner diameter of the rigid portion and/or the distal tip end 4 of the elongate body to the smaller inner diameter of the atraumatic tip 7 (FIG. 15). As such, the taper also provides a smooth transition or lead-in (reducing "catch" points) for the obturator or other surgical instruments being inserted into the cannula and through the tip.

The greater or larger ultimate elongation of the tip relative to the rigid portion 5 of the cannula 3, as noted above, also assists in the interference fit between the tip and the inserted obturator. The tip 7 is allowed to stretch to accommodate an obturator having an outer diameter larger than the inner diameter of the tip, thereby providing a tight instrument seal and a smooth transition between instrument and tip and tip to cannula. The difference ensures that the tip stretches or expands relative to the cannula allowing the tip to allow passage of the inserted surgical instrument, e.g., a laparoscope, obturator, and others, having an outer diameter larger than the inner diameter of the tip. An interference fit and/or instrument seal is thereby provided with the tip and the inserted surgical instrument.

The cannula 3 with the atraumatic elastomeric tip 7 in one aspect is formed of reusable materials to enable the product to be autoclave sterilized and re-used. Reusable materials for the cannula and elastomeric tip in one aspect can be polysulfone, polyetherimide, polyethersulfone, silicone, and polyisoprene. The cannula 3 with the atraumatic elastomeric tip 7 in one aspect is formed of stainless steel with a bonded elastomeric tip formed of silicone or polyisoprene to enable the product to be autoclave sterilized and re-used.

The cannula 3 with the atraumatic tip 7 in one aspect has a short length over-molded section at its distal tip. The short length over-molded section can provide for an atraumatic elastomeric cannula tip, yet utilize no or minimal column strength or less axial column strength as compared to a longer length over-molded section. The length of the shortened section in one aspect varies from 0.025" to 0.250".

Figure 11:
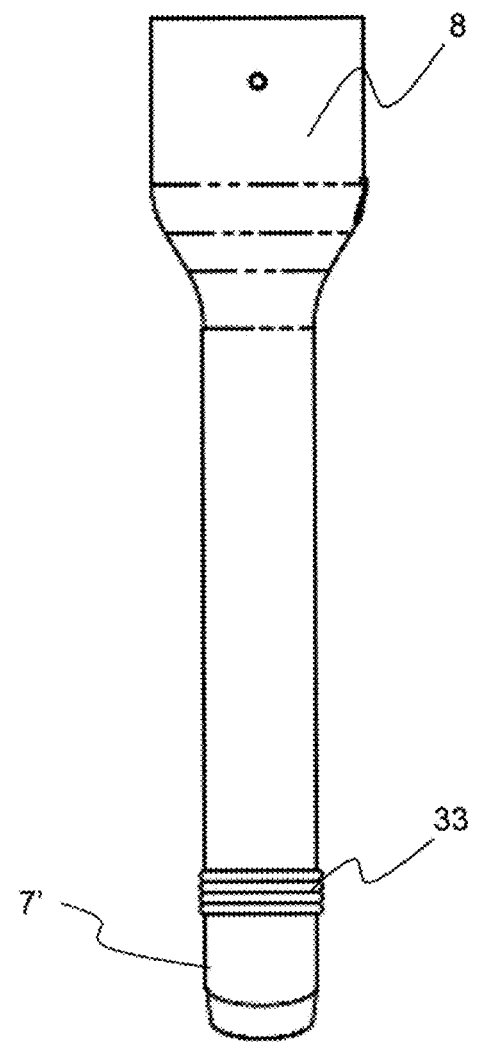
FIG. 11 is a side view of a trocar cannula in accordance with various aspects of the present invention.

In FIG. 11, the cannula 3 in one aspect has a flexible elastomeric joint 33 between the rigid portion 5 of the cannula and the distal tip 7' of the cannula. The distal tip of the cannula in one aspect is either flexible or rigid. The flexible joint 33 allows the distal tip of the cannula to deflect in response to contact between, for example, body tissue or an instrument thereby preventing potential trauma to the body tissue or potential damage to the instrument. The flexible joint 33 in one aspect has a bellows configuration with a minimal axial length. The minimal axial length of the flexible joint 33 in combination with a rigid or semi-rigid distal tip 7 in one aspect can provide the cannula 3 with greater column strength as compared to a cannula with an over-molded elastomeric tip. The flexible joint in one aspect is formed from silicone, polyurethane, Kraton® thermoplastic elastomers, C-Flex® thermoplastic elastomers, Versaflex® thermoplastic elastomers, polyisoprene, Santoprene® thermoplastic elastomers, Carbothane® thermoplastic polyurethanes, copolymer/mineral oil gels, or natural rubber.

Figure 12:
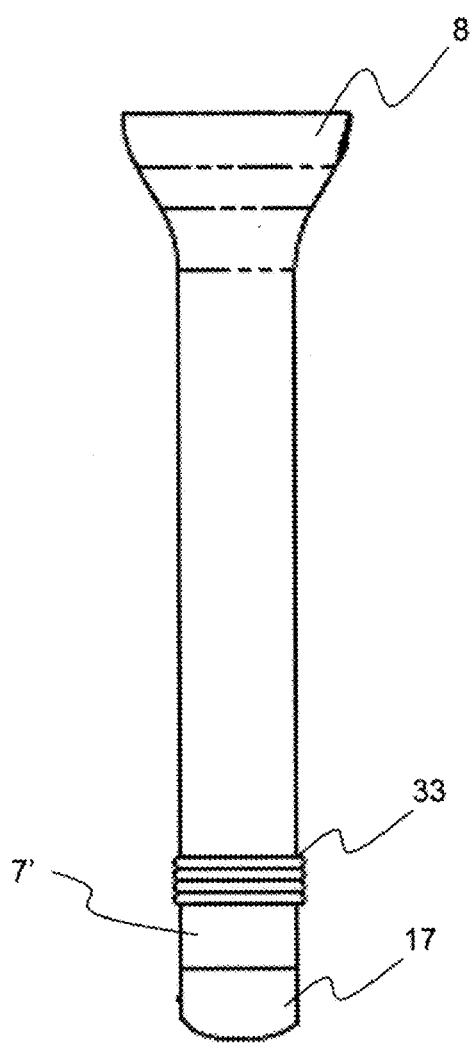
FIG. 12 is a side view of a trocar cannula in accordance with various aspects of the present invention.
Figure 13:
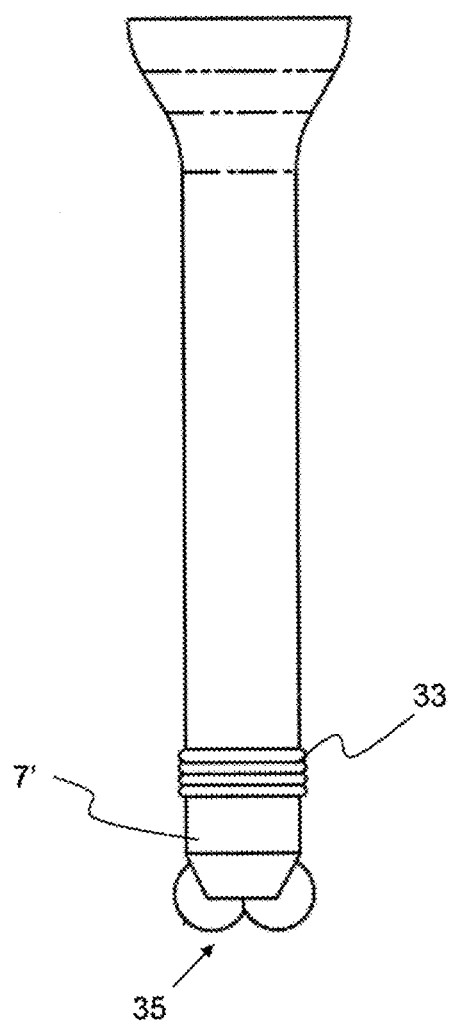
FIG. 13 is a side view of a trocar cannula in accordance with various aspects of the present invention.

In FIG. 12, in one aspect, the cannula 3 with the flexible joint 33 has a seal 35 formed of a gel material located at the distal tip 7' of the cannula. The seal 35 in one aspect is configured to maintain a seal in the absence of inserted instrumentation and the seal, in one aspect, is configured to maintain a seal in the presence of inserted instrumentation. The flexible joint 33 allows the seal 35 and the distal tip 7' to pivot in response to the lateral movement of inserted instrumentation to ensure that a seal 35 is maintained during off-axis movement of the instrumentation. The seal 35 could be formed of a single piece component with the gel for example shaped as a disc with a slit in the center of the disc. In one aspect, as shown in FIG. 13, seal 35' is formed of two opposed gel rollers, such that instrumentation would be inserted between the rollers. The cannula 3 with the seal 35 can also be formed without the flexible joint 33. The elongation and sealing properties of the gel material can enable a seal to be maintained during off-axis movement of inserted instrumentation. The gel material in one aspect is formulated of an SEBS (Styrene Ethylene Butylene Stryrene) copolymer and a mineral oil.

Figure 14:
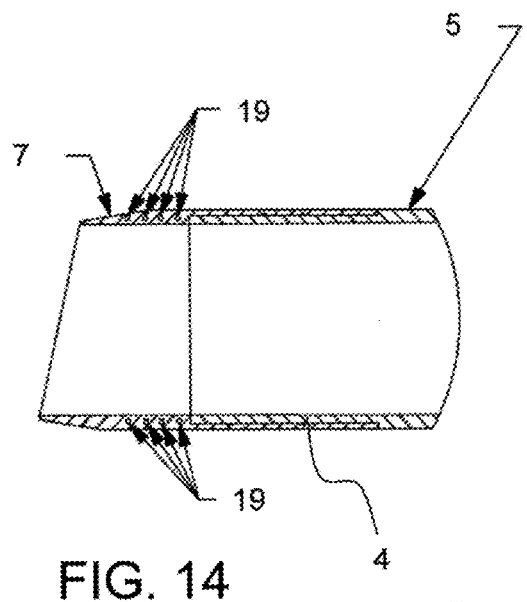
FIG. 14 is an enlarged cross-sectional side view of a portion of a trocar cannula in accordance with various aspects of the present invention.

Referring now to FIG. 14, the atraumatic elastomeric cannula tip 7 in one aspect is formed with an internal wire form 19 to provide greater rigidity and column strength as compared to a cannula tip without an internal wire form. The wire form 19 in one aspect is configured in the shape of a coil spring and a polymer is fused or over-molded over the wire form resulting in a cannula tip 7 with an embedded wire form. The wire form in one aspect also comprises a series of wires radially spaced and embedded within the atraumatic elastomeric cannula tip.

Accordingly, a trocar cannula with an atraumatic tip is provided. Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A surgical access system comprising:
a trocar cannula comprising:
a rigid elongate body having a proximal enlarged end and a distal tip end with a lumen extending from the proximal end to the distal end for inserting and removing surgical instruments through the lumen; and
an atraumatic tip integrated with and extending from the distal tip end of the elongate body, the atraumatic tip being more compliant than the elongate body and formed from a material different from the elongate body; and
wherein the rigid elongate body comprises a plurality of annular projections formed on the distal tip end of the elongate body such that the plurality of annular projections provides a mechanical interlock on the elongate body at an interface with the atraumatic tip such that the atraumatic tip is restricted from moving in a proximal and a distal direction relative to the rigid elongate body; and
an obturator insertable through the lumen of the elongate body and the atraumatic tip, the atraumatic tip having an inner diameter less than an outer diameter of the obturator.

2. The surgical access system of claim 1 further comprising a distal portion of the atraumatic tip of the trocar cannula having a wall thickness substantially similar to a wall thickness of a proximal portion of the elongate body.

3. The surgical access system of claim 1 wherein the atraumatic tip of the trocar cannula has an inner diameter that is less than an inner diameter of the elongate body.

4. The surgical access system of claim 1 wherein the atraumatic tip of the trocar cannula is over-molded onto the distal tip end of the elongate body.

5. The surgical access system of claim 1 wherein the distal tip end of the rigid elongate body of the trocar cannula has a wall thickness smaller than remaining portions of the elongate body.

6. The surgical access system of claim 1 further comprising a proximal portion of the atraumatic tip of the trocar cannula having a wall thickness substantially similar to the distal tip end of the elongate body.

7. The surgical access system of claim 1 further comprising an embedded wire within the atraumatic tip of the trocar cannula.

8. The surgical access system of claim 1 wherein the elongate body of the trocar cannula has an ultimate elongation less than an ultimate elongation of the atraumatic tip.

9. The surgical access system of claim 1 further comprising a trocar seal housing connected to the proximal enlarged end of the elongate body of the trocar cannula.

10. The surgical access system of claim 1, wherein the atraumatic tip of the trocar cannula has a flexural modulus that is less than 10,000 psi.

11. The surgical access system of claim 1, wherein the atraumatic tip of the trocar cannula is formed of a transparent material.

12. The surgical access system of claim 1, wherein the atraumatic tip of the trocar cannula has a length within the range of approximately 0.25 inches to 1 inches.

13. The surgical access system of claim 1, wherein the plurality of annular projections comprises a plurality of annular barbs.

14. A surgical access system comprising:
a trocar cannula comprising:
a rigid elongate body having a proximal enlarged end and a distal tip end with a lumen extending from the proximal end to the distal end for inserting and removing surgical instruments through the lumen; and
an atraumatic tip integrated with and extending from the distal tip end of the elongate body, the atraumatic tip being more compliant than the elongate body and formed from a material different from the elongate body; and
wherein the rigid elongate body comprises a plurality of annular projections formed on the distal tip end of the elongate body such that the plurality of annular projections provides a mechanical interlock on the elongate body at an interface with the atraumatic tip such that the atraumatic tip is restricted from moving in a proximal and a distal direction relative to the rigid elongate body; and
a laparoscope insertable up to a proximal portion of the atraumatic tip, the atraumatic tip being transparent.

15. The surgical access system of claim 14 further comprising a distal portion of the atraumatic tip of the trocar cannula having a wall thickness substantially similar to a wall thickness of a proximal portion of the elongate body.

16. The surgical access system of claim 14 wherein the atraumatic tip of the trocar cannula is over-molded onto the distal tip end of the elongate body.

17. The surgical access system of claim 14 wherein the distal tip end of the rigid elongate body of the trocar cannula has a wall thickness smaller than remaining portions of the elongate body.

18. The surgical access system of claim 14 further comprising a proximal portion of the atraumatic tip of the trocar cannula having a wall thickness substantially similar to the distal tip end of the elongate body.

19. The surgical access system of claim 14 further comprising an embedded wire within the atraumatic tip of the trocar cannula.

20. The surgical access system of claim 14 wherein the atraumatic tip of the trocar cannula has an inner diameter that is less than an inner diameter of the elongate body.

21. The surgical access system of claim 4 wherein the elongate body of the trocar cannula has an ultimate elongation less than an ultimate elongation of the atraumatic tip.

22. The surgical access system of claim 14 further comprising a trocar seal housing connected to the proximal enlarged end of the elongate body of the trocar cannula.

23. The surgical access system of claim 14, wherein the atraumatic tip of the trocar cannula has a flexural modulus that is less than 10,000 psi.

24. The surgical access system of claim 14, wherein the atraumatic tip of the trocar cannula has a length within the range of approximately 0.25 inches to 1 inches.

25. The surgical access system of claim 14, wherein the plurality of annular projections comprises a plurality of annular barbs.

26. A trocar cannula comprising:
a rigid elongate body having a proximal enlarged end and a distal tip end with a lumen extending from the proximal end to the distal end for inserting and removing surgical instruments through the lumen; and
an atraumatic tip integrated with and extending from the distal tip end of the elongate body, the atraumatic tip being more compliant than the elongate body and formed from a material different from the elongate body; and
wherein the rigid elongate body comprises a plurality of annular projections formed on the distal tip end of the elongate body such that the plurality of annular projections provides a mechanical interlock on the elongate body at an interface with the atraumatic tip such that the atraumatic tip is restricted from moving in a proximal and a distal direction relative to the rigid elongate body, wherein the lumen of the rigid elongate body has a first inner diameter, and wherein the atraumatic tip has a second inner diameter defined by a tapered narrowing transitioning from a relatively large proximal inner diameter corresponding to the first inner diameter of the rigid elongate body to a relatively small distal inner diameter.

27. The cannula of claim 26 wherein the atraumatic tip is over-molded onto the distal tip end of the elongate body.

28. The cannula of claim 26 wherein the distal tip end has a wall thickness smaller than remaining portions of the elongate body.

29. The cannula of claim 26 further comprising a proximal portion of the atraumatic tip having a wall thickness substantially similar to the distal tip end of the elongate body.

30. The cannula of claim 26 further comprising an embedded wire within the atraumatic tip.

31. The cannula of claim 26 wherein the elongate body has an ultimate elongation less than an ultimate elongation of the atraumatic tip.

32. The cannula of claim 26 further comprising a trocar seal housing connected to the proximal enlarged end of the elongate body.

33. The cannula of claim 26, wherein the atraumatic tip has a flexural modulus that is less than 10,000 psi.

34. The cannula of claim 26, wherein the atraumatic tip is formed of a transparent material.

35. The cannula of claim 26, wherein the atraumatic tip has a length within the range of approximately 0.25 inches to 1 inches.

36. The cannula of claim 26, wherein the plurality of annular projections comprises a plurality of annular barbs.

* * * * *